US00PP24293P2

(12) United States Plant Patent
Jansen

(10) Patent No.: US PP24,293 P2
(45) Date of Patent: Mar. 4, 2014

(54) ***PENSTEMON* PLANT NAMED 'WATERMELON TAFFY'**

(50) Latin Name: ***Penstemon* hybrid**
Varietal Denomination: Watermelon Taffy

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 51 days.

(21) Appl. No.: 13/573,067

(22) Filed: Aug. 16, 2012

(51) Int. Cl.
*A01H 5/00* (2006.01)

(52) U.S. Cl.
USPC ..... Plt./465

(58) Field of Classification Search
USPC ..... Plt./465
See application file for complete search history.

*Primary Examiner* — Annette Para
(74) *Attorney, Agent, or Firm* — Klarquist Sparkman, LLP

(57) ABSTRACT

A new and distinct cultivar of *Penstemon* plant characterized by large dark pink edged flowers with a clear white throat, long bloom time, a compact, upright, well branched habit, with multiple crown from the base, clean-looking, deep green, attractive foliage, and excellent vigor.

1 Drawing Sheet

Botanical denomination: *Penstemon* hybrid.
Variety designation: 'Watermelon Taffy'.

BACKGROUND OF THE INVENTION

The present invention relates to a new and distinct cultivar of *Penstemon,* given the name, 'Watermelon Taffy'. *Penstemon* is in the family Scrophulariaceae. This plant originated a controlled breeding plan to create a compact, upright, large flowered series. The exact parents are unknown, unnamed proprietary plants. This cultivar was selected for its compact growing habit, large flowers in dense clusters, long flowering time, vigor, and clean attractive look. It is an ideal plant for a sunny border in full sun.

Compared to *Penstemon* 'Strawberry Taffy' (U.S. Plant Pat. No. 22,569), the new cultivar has a clear white throat rather than the maroon bee tracks on the bottom of the throat.

Compared to *Penstemon* 'Pheni Pinka' (U.S. Plant Pat. No. 17,912), the new cultivar has a smaller habit and flowers that are darker pink with no red markings on the throat.

*Penstemon* 'Watermelon Taffy' is uniquely distinguished by its:

1. large dark pink edged flowers with a clear white throat,
2. long bloom time,
3. compact, upright, well branched habit, with multiple crown from the base,
4. clean-looking, deep green, attractive foliage, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the new cultivar in the garden in full bloom in mid July in Canby, Oreg.

DETAILED PLANT DESCRIPTION

The following is a detailed description of the new *Penstemon* cultivar based on observations of two-year-old specimens grown outside in the ground in the garden in Canby, Oreg. in late July. The color descriptions are all based on The Royal Horticultural Society Colour Chart, 5$^{th}$ edition.

Plant:

*Type.*—Herbaceous perennial.
*Form.*—Upright, branching.
*Cold hardiness.*—USDA Zone 7-10.
*Size.*—Grows to 37 cm wide and 70 cm high.
*Vigor.*—Excellent.
*Stem number.*—About 18 stems from the crown.
*Stem.*—Upright, grows to 52 cm long and 6 mm wide (at the base), glabrous, internodes grow to 5 cm long, Yellow Green 145C.
*Rooting.*—Plants root easily from stem cuttings.

Leaf:

*Type.*—Simple.
*Arrangement.*—Opposite.
*Shape.*—Lanceolate.
*Venation.*—Pinnate, main vein on top and bottom side Yellow Green 145C.
*Margins.*—Entire.
*Apex.*—Acuminate.
*Base.*—Sessile.
*Blade size.*—Grows to 11.2 cm long and 2.1 cm wide.
*Surface texture.*—Glabrous on both sides.
*Leaf color.*—Topside Green 137A, bottom side closest to Yellow Green 146B.

Inflorescence:

*Type.*—Terminal, many flowered, dense thyrse.
*Number of flowers per inflorescence.*—22 on average.

*Size of inflorescence.*—Grows to 23 cm long and 9 cm wide.

*Peduncle.*—Grows to 5 cm long and 4 mm wide, glabrous, Yellow Green 145B.

*Pedicel.*—Grows to 10 mm long and 1 mm wide, pubescent, Yellow Green 147C.

*Bloom period.*—Mid June to frost in October in Canby, Oreg. if spent flowers are removed.

Flower bud:

*Size.*—3.2 cm long and 14 mm wide.

*Description.*—Closed tubular, bulging, flattened ventrically.

*Color.*—White 155A except Red 51A on lobes and 51C tinted on top.

Flower:

*Type.*—Zygomorphic, perfect.

*Shape.*—Tubular, bilabiate.

*Size.*—Grows to 4 cm long and 4 cm wide.

*Corolla description.*—Grows to 4 cm long and 4 cm wide; tube is funnel-form in the calyx for 6 mm long and 5 mm wide, inflating for 25 mm long to 17 mm wide, flaring into 5 lobes, the two smaller top lobes flare back (13 mm wide and to 12 mm deep) and two larger lateral lobes flare out (18 mm wide and 11 mm deep), and the lower lobe flares down (16 mm wide and 12 mm deep), lobe margins entire to slightly jagged, tips obtuse; outside glandular pubescent, inside sparsely pubescent; outside color White NN155B on tube except on top where Red Purple N57C, lobes Red Purple 61A ; inside color on edges Red Purple 58B blending to Red 55A on the lobes for 5 to 7 mm then White NN155C.

*Calyx description.*—10 mm deep and 7 mm wide, 5 overlapping lobes cut to the base, each lobe broadly ovate in shape, 10 mm deep and 6 mm wide, margins entire, tip acute, base cuneate, Yellow Green 146C, glabrous inside and pubescent outside.

*Pistil description.*—1, 33 mm long, ovary 6 mm long and 3 mm wide, Yellow Green 145A; style 27 mm long and less than 1 mm wide, style Red Purple 61A on bottom half and White NN155C on top half, stigma White NN155C.

*Stamen description.*—5, one sterile without an anther, held within the corolla 30 mm long, filaments 27 to 31 mm long and White NN155C, anthers 3 mm wide and 3 mm deep, Purple N79A, pollen White NN155C.

*Fragrance.*—None.

*Lastingness.*—A flower lasts 5 to 6 days.

Fruit:

*Type.*—Capsule.

*Fertility.*—Good.

*Size.*—1.2 cm deep and 4 mm wide.

*Color.*—Brown 200A to B.

Seed:

*Shape.*—Irregular.

*Size.*—2 mm long.

*Color.*—Brown 200A.

Pests and diseases: The new cultivar is typical to the genus. No known resistances to pests or diseases. No problems have been found in Canby, Oreg.

I claim:

1. A new and distinct *Penstemon* plant as herein illustrated and described.

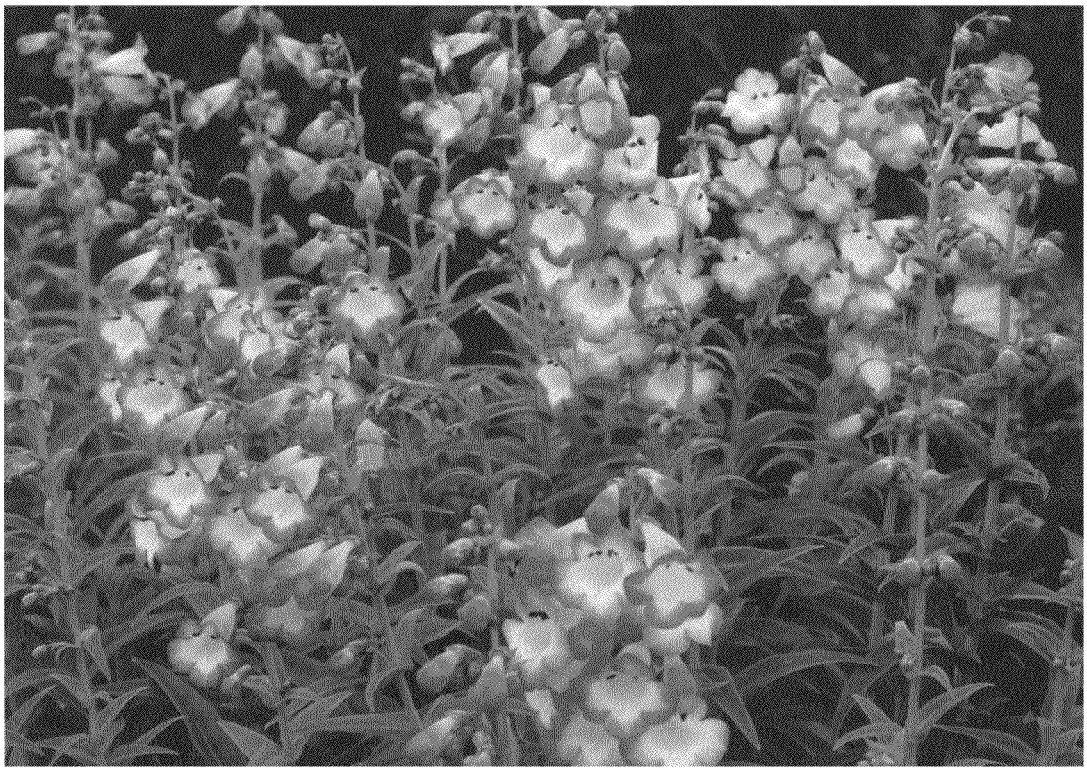

* * * * *